United States Patent [19]

Fleury, Jr.

[11] 4,326,530

[45] Apr. 27, 1982

[54] SURGICAL SNARE

[76] Inventor: George J. Fleury, Jr., 1005 Abbey Way, McLean, Va. 22101

[21] Appl. No.: 127,321

[22] Filed: Mar. 5, 1980

[51] Int. Cl.$^3$ .............................................. A61B 17/39
[52] U.S. Cl. .............................. 128/303.14; 128/320
[58] Field of Search ...................... 128/303.14, 303.15, 128/303.16, 320, 309, 307, 303 R, 328, DIG. 9

[56] References Cited

U.S. PATENT DOCUMENTS

| | | | |
|---|---|---|---|
| 3,791,387 | 2/1974 | Itoh | 128/320 |
| 3,955,578 | 5/1976 | Chamness et al. | 128/303.15 |

FOREIGN PATENT DOCUMENTS 926931  10/1947  France .............................. 128/307

*Primary Examiner*—Michael H. Thaler
*Attorney, Agent, or Firm*—Eric P. Schellin

[57] ABSTRACT

A surgical instrument for removing cellular tissue from the body cavities arranged to shape a loop easily by using an elongated cable. The cable is folded essentially in the middle intermediate the ends thereof. The thusly folded cable is positioned internally of an elongated open ended sheath. Manipulative structure is provided at the proximal end for selectively reciprocatively sliding one or both of end portions of the cable whereby a loop may be formed externally of the other end of the sheath. The structure when manipulated provides a controlled configuration of the loop.

8 Claims, 7 Drawing Figures

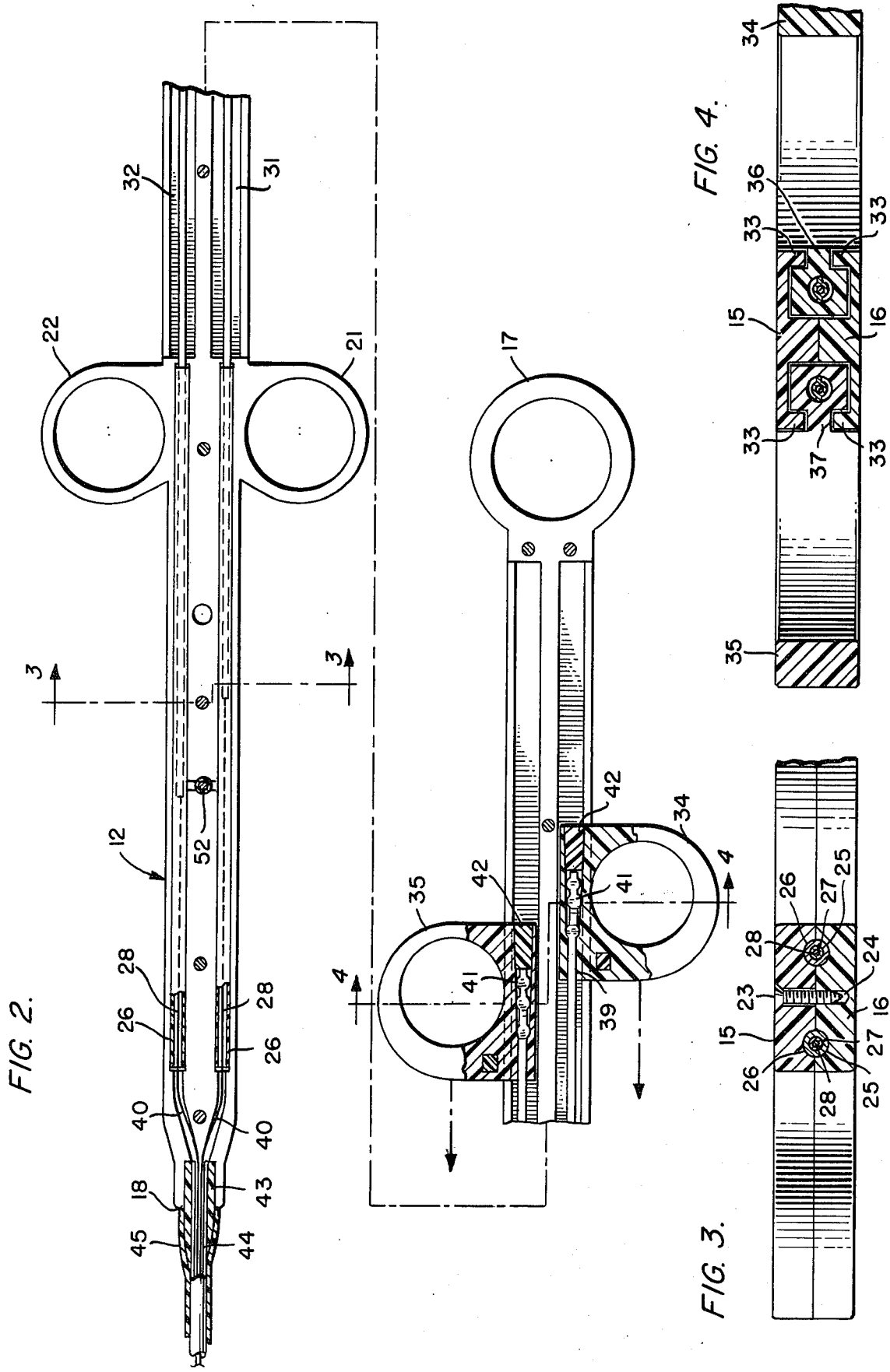

SURGICAL SNARE

BACKGROUND OF THE INVENTION a. Field of the Invention

The present invention relates to a surgical snare for performing a procedure known as colonoscopic polypectomy.

b. Description of the Prior Art

Various types of surgical snares have been employed for a number of years to remove polyps from the colon and rectum. Advances have been made whereby surgical snares have been introduced through the elongated bore of a colonoscope. A colonscope is a fairly multiconduited tubular member useful for inserting into a bowel for examination thereof internally. It possesses a fiber optics system whereby light may be transmitted to the distal end thereof for illumination of a site. Similarly, the fiber optic system includes the means to view the thusly illuminated site.

The surgical snare comprises an elongated flexible sheath connected at its proximal end to an operating handle. Extending through the sheath is an elongated flexible cable, the proximal end is connected to means in a handle whereby the operating loop can be extended beyond an open end of the sheath and may be withdrawn thereinto. The operating loop terminates as a fold which is that portion that extends beyond the sheath when it is protracted. In other words there is a loop connected to the distal end portion of the cable.

The loop comprises the snare. The loop can be opened or closed by the operator of the snare to the extent that he operates a movable portion of an operating means to extend forwardly or to withdraw the folded portion of the cable.

When the cable is in its protracted position a loop is formed forward and external of the sheath. The loop is formed due to the resiliency of the cable especially due to the fold which tends to want to unfold thereby forming a loop. The operator is thereby in a position to play the loop over and around a polyp required to be removed. The cable may then be retracted resulting in diminishing the overall size of the loop as the cable is withdrawn into the sheath. Closing off the loop entirely will sever the polyp. To prevent bleeding from the blood vessels at the remaining severed surface a coagulating radio frequency current is applied to the cable and thence to the loop as the patient is grounded in a conventional manner. The radio frequency is applied just prior and during the severing procedure.

The deficiencies inherent in the prior art instruments can be identified as follows:

1. A large proportion of the loop must be protracted from the sheath before it can define an open configuration. This characteristic makes it difficult for the operator to effectively adjust the size of the loop to the size of the polyp being removed and to the working area available. A large loop must be formed to remove even a small polyp. In order to open the loop adequately it is often necessary to advance the loop blindly beyond the space within the bowel visible to the operator, a potentially dangerous manuever. The large loop in unwieldy and often difficult to maneuver in a small space.

2. After repeated use the resiliency of the wire loop diminishes and a satisfactory configuration is no longer achieved when the loop is protracted beyond the sheath.

3. The loop can be formed in one plane only which often makes it difficult to maneuver the loop over the polyp.

These deficiencies have been partially overcome by later changes in snare design.

Komiya in U.S. Pat. No. 3,903,892 describes a snare in which the configuration of the loop can be controlled to a limited degree by differential protraction of the two members of the loop, achieved by the use of an elongated spring within the sheath.

Chamness et al in U.S. Pat. No. 4,955,578 described a snare in which the plane of the loop can be altered by rotating the operating loop assembly about its long axis. This snare usually requires a larger sheath than can be accomodated by the commonly used colonoscopes and does not correct the loop configuration deficiencies of the standard snares.

Shinya and Wolf (Hospital Practice, September 1975, Page 72) describe a simple snare consisting of a braided steel wire doubled over and inserted through a Teflon catheter of 2.7 mm. outside diameter. Both segments of the cable extend the full length of the sheath and each segment can be independently protracted or retracted by the fingers of the operator of the snare. This device permits the formation of a loop varying in size from very small to very large, the plane of which can be adjusted from one that is parallel to the axis of the sheath to one that is at right angles to that axis. These capabilities provide a decided advantage in the often difficult task of accurately maneuvering the loop over the head of the polyp. They also make it possible to open the loop and remove it from the polyp if repositioning should seem advisable. However, this device requires the services of a highly trained assistant who must have at his disposal a teaching attachment (auxiliary eyepiece) for the colonoscope. This requirement renders this very versatile snare inaccessable to most endoscopists, who do not have available the services of such a highly trained assistant.

SUMMARY OF THE INVENTION

This invention relates to a surgical snare comprising an elongated electrically insulating flexible sheath within which is movably situated an electrically conductive snare loop means consisting of a single piece of wire, doubled on itself with a distal cusp, the free ends passing through the sheath and being individually movable forward and backward by mechanical means provided in the operating portion attached adjacent to the proximal end of the sheath. The means for moving the individual end portions of the wire, in addition to being independently controllable, are provided with a locking device permitting them to be moved in unison and in a constant specific spatial relation with each other during the actual cutting operation of the snare.

The electrical current is transmitted to the snare wire by a novel method whereby a fixed segment of steel tubing serves as a brush to conduct the current to a telescoping smaller movable segment of steel tubing containing and retaining the wire.

DESCRIPTION OF THE INVENTION

FIG. 2 is a top plan view of the manipulative portion of the device taken along line 2—2 of FIG. 1.

FIG. 3 is an enlarged cross-sectional view of the said manipulative portion of the device taken along line 3—3 of FIG. 2.

FIG. 4 is an enlarged cross-sectional view of the said manipulative portion of the device taken along line 4—4 of FIG. 2.

DETAILED DESCRIPTION OF THE INVENTION

Figure 1:
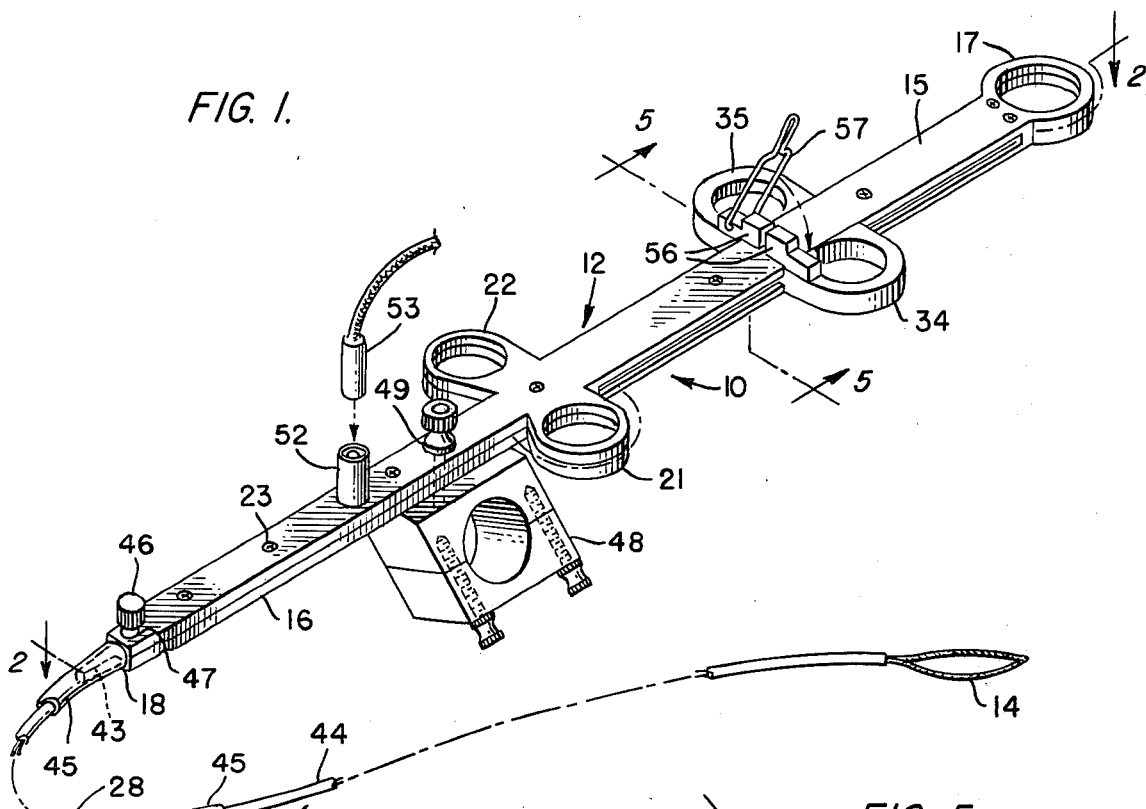
FIG. 1 is a perspective view of the device of the present invention with portions broken away and with the operating loop in a partially protracted position.

Turning now to the drawings in detail the device 10, generally, of the present invention may be seen in FIG. 1. It will be noted that the device 10 has a housing having an elongated body portion which will hereinafter be termed the manipulative portion 12. Extending from one end of said manipulative portion 12 is a flexible elongated tubular portion, generally, 13 having an open end through which a loop 14 may desirably be protracted. It should be noted that the elongated body portion may be fabricated of a relatively rigid polymeric material although other suitable materials are contemplated. The said portion may be machined from suitable pieces or may result from conventional molding techniques.

The manipulative portion 12 is constructed of an upper elongated part 15 and a lower elongated part 16. In the embodiment shown by FIG. 1 the two parts are essentially mirror images of one another. As such the outward appearance is for manipulative portion 12 to possess a convenient thumb retaining ring 17 at one end of the manipulative portion 12 in the same plane as the major plane of the manipulative portion 12. The opposite end has extending therefrom through a suitable opening 18 the aforementioned tubular portion 13.

It will be seen that a set of additional finger retaining rings 21 and 22 are situated intermediate the ring 17 and the other end of the manipulative portion 12. One of these rings 21 is positioned on one side of the manipulative portion 12 while the other ring 22 is located on the opposite side. Both rings will be seen to be in the same plane as the major plane of the manipulative portion 12.

It is pointed out that in the embodiment herein discussed the aforementioned finger retaining rings are integral for one portion with the upper elongated part 15 and integral for another portion with the lower elongated part 16. However, it should be appreciated that in alternative embodiments neither the said upper nor the said lower parts need contribute to the integral provision of said finger retaining rings. Such rings may be, in fact, separately constituted and may be then subsequently affixed by suitable means, such as by adhesive or the like.

Before providing additional details of construction, it is pointed out that the aforementioned thumb and finger rings may not be necessarily complete rings. The retaining thumb and finger retaining means may consist of partially embracing means such as arcuate extensions that are usefully applicable for the purpose herein intended.

With regard to the manipulative portion 12 it is taught herein that the upper elongated part 15 and the lower elongated part 16 may be secured in a laminate fashion as by small spaced self tapping screws 23 in spaced suitably drilled bores 24 perpendicular to the major plane of the said manipulative portion 12 essentially axially thereof as can be more readily discerned from the FIG. 1. Of course, it is within the purview of the instant matter that the two elongated parts may be permanently laminated as by an adhesive or heat welding. A permanent lamination may be found efficacious especially when it is desirable to fabricate a device that is considered to be essentially disposable after a single use.

When the manipulative portion 12 is assembled as shown in FIG. 1 the said portion includes two elongated bores 25 in that part thereof between the finger rings and the end carrying the opening. The bores are created by producing elongated channels on a downwardly facing surface of one confronting upper elongated part 15 and another on a surface of the other confronting upwardly facing elongated part 16. When the two elongated parts are assembled the bore 25 is formed as can be seen from FIG. 3. The bore is supplied with a fixed elongated stainless steel conduit 26 (I.D. 0.047", O.D. 0.065"). FIG. 3 is shown with an inner telescoping concentric stainless steel tube 27 (I.D. 0.027", O.D. 0.042") slidably positioned within conduit 26. Internally of said tube 27 is an elongated braided or twisted stainless steel small diameter cable 28, more about which will be stated below.

The manipulative portion 12 located along each side thereof between the thumb ring 17 and the aforementioned finger rings 21 and 22 is supplied with an elongated guide channel 31 and 32, respectively. Each channel possesses confronting side rails 33. For a view of this feature of the device of the present invention attention is directed to FIGS. 4 and 5.

Each of the channels is supplied with a slide means 34 and 35, respectively. Each slide means has a T-shaped portion 36 and 37, respectively, and has a configuration adapted and constructed to be able to slide to and fro in each of their respective channels. Each T-shaped portion 36 and 37, respectively, is a part of an extending finger retaining ring disposed in a similar plane with respect to the other thumb and finger retaining means discussed in detail in the above.

Essentially, centrally each T-shaped portion of each slide means has a bore 39 therethrough as can be readily seen from FIG. 2. Each bore 39 is designed to be larger in the direction of the thumb ring. The purpose therefore is now explained. The forementioned cable 28 employed in carrying out the principles of the present invention is in fact a single long cable doubled on itself with the resultant ends terminating at one end of each of said tubes 27.

Each of the ends of the cables are supplied with a conventional crimping collar 41 and crimped. Additionally, the end portions of tubes 27 are crimped to each of the cables whereby the crimp is in tandem displacement with the collar 41. The crimping collar 41 serves to secure the end portions of the cable but also by being somewhat wider than the more constricted portion of the bores 39 the tubes 27 and cable are secured. From FIG. 2 it will be seen that the wider end portion of the respective bores are occluded with plugs 42 thereby the tubes 27 carrying the wire cannot project from the slide means.

From FIG. 2 it will be seen that the forward end of the manipulative portion 12 has converging bores 40 so that the two cables as they project through the opening 18 are now in side by side relationship. A suitably positioned short sheath assembly collar 43 is positioned about an elongated Teflon sheath 44 adapted and constructed to surround the two end portions of the cable 28. From FIGS. 1 and 2 it will be seen that both the short sheath assembly collar 43 and the sheath 44 are embraced concentrically by another more rigidifying Teflon sheath 45 appropriately flared at one end to embrace both the collar 43 and the underlying sheath and cables. This rigidifying sheath 45 is designed to control the bending of the sheath 44 and the cables contained therein so that the assembly does not become unduly kinked proximate the end of the manipulative portion 12, therefore need not be particularly lengthy. The sheath assembly collar 43 is adhesively secured to the end portion of sheath 44. The said collar 43 has a short perpendicular bore. The bore is designed to be aligned with a threaded bore 47 near the proximal end portion of the manipulative portion 12 through which a thumb set screw 46 may be screwed to retain the sheath 44 carrying the cable. The thumb set screw 46 permits easy disassembly as desired for cleaning.

Figure 7:
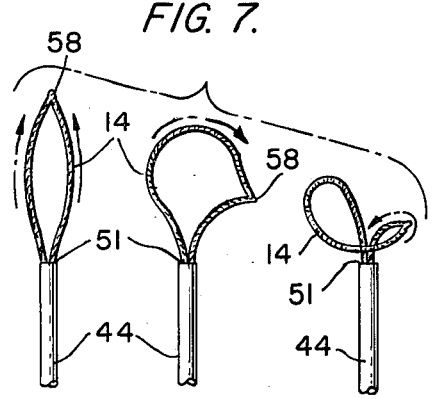
FIG. 7 is a view of one end portion of the device illustrating effectively various loop formations.

The sheath 44 carrying the cable is permitted to extend for about two meters. The sheath 44 terminates with an opening 51 through which the doubled or folded portion of the cable may be protracted to provide a loop 14, as can be seen from FIGS. 1 and 7.

As will be appreciated the to and fro movement of the slide means 34 and 35 constituting the terminus of the cable is the controlling factor as to whether or not the doubled cable projects from the end of the sheath or whether it is withdrawn. When the slide means are positioned substantially rearwardly proximately the thumb retaining ring 17 the relative length of the cable and the sheath 44 are such whereby the doubled cable is completely withdrawn into the sheath 44 and no external loop 14 is present. By sliding the slide means 34 and 35 in the opposite direction towards the finger retaining rings 21 and 22, the doubled cable is projected externally of said sheath 44.

Figure 5:
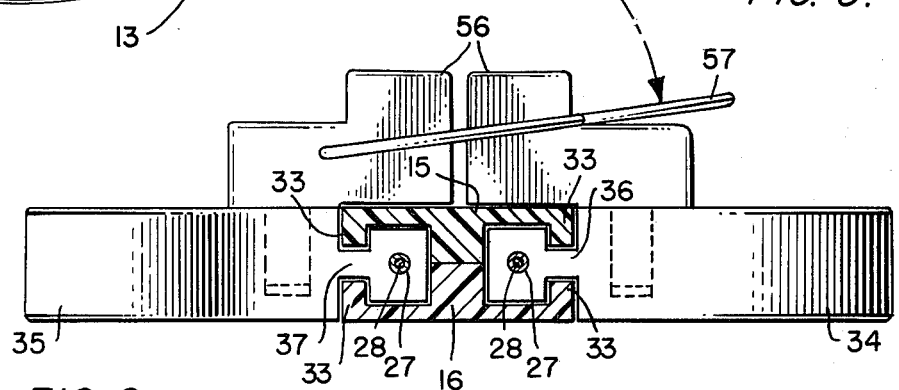
FIG. 5 is an enlarged cross-sectional view of the said manipulative portion of the device taken along line 5—5 of FIG. 1.
Figure 6:
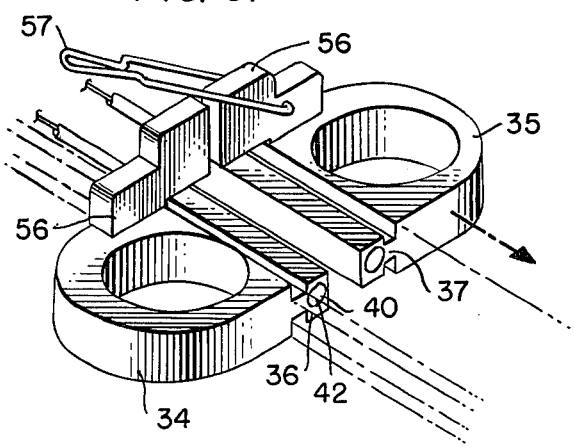
FIG. 6 is a perspective fragmentary view locking forward of the manipulative portion of the device.

In presenting the loop 14, it will be usually desirable to move both the slide means in unison. To assist in such a movement, each of the slide means 34 and 35 is supplied with an L-shaped locking block 56 as can be seen in FIGS. 1, 5 and 6. The blocks 56 are in a mirror confrontation. They may be press fitted into each of the slide means or they may be secured thereto as by adhesives, screws and the like. One block 56 is hingedly supplied with a locking lever of wire 57 having generally a U-shaped configuration whereby when it is in the securing mode it tethers together the upstanding portions of the blocks 56 and thereby each of the slide means. When the wire 57 is in the other mode the blocks are unhooked permitting independent reciprocating sliding movement, as desired. FIGS. 1 and 6 show the slide means 34 and 35 capable of independent motion while FIG. 5 shows the slide means 34 and 35 capable of only motion in unison.

As cauterizing r.f. energy is to be supplied to the loop 14 through the cable, an electrical connector 52 is supplied to the upper surface of the manipulative portion 12, as in FIG. 1. The connector has suitable electrically conducting means supplied between the said connector 52 and one or preferably both of the conduits 26 and therein to tube 27 to which the cable ends are connected. FIG. 1 shows an easily plug in jack 53 exploded from the connector 52.

In practice, a colonoscope will be first positioned at the site of a bowel that reveals through the fiber optic means the presence of a polyp. The manipulative portion 12 has a two part clamping block 48 optionally secured to it by screw 49 as in FIG. 1 whereby the device of the present invention may be secured to the colonoscope. The sheath 44 carrying the retracted cable is then threaded through an elongated bore in the colonoscope provided for this purpose. It is inserted to a point where it is permitted to project beyond the end of the colonoscope where it is also in view through the fiber optic system. At which point the slide means are moved forwardly in unison to a point represented diagrammatically as at FIG. 1 whereby the loop 14 of folded cable projects as shown. A loop 14 will form due to the natural and expected relaxation of tension supplied by the immediate folded end portion 58 of the doubled over cable when it protracts beyond the sheath 44. The loop 14 will have somewhat the configuration of the left most embodiment of FIG. 7. At this point the hinged wire 57 is moved to unshackle the slide means 34 and 35. When the slide means 34, on the left side (looking forward) of the manipulative portion 12, as in FIG. 6, is moved forward a portion of the cable is protracted from sheath 44, to produce a movement of the folded end portion 58 to the right with a concomitant opening of the loop 14. This phase of the loop 14 formation is shown by the middle figure of FIG. 7. A withdrawal of slide means 35 on the right side will result in a three dimensional movement of the loop as graphically expressed by the third figure of FIG. 7.

Desirable loop formation will depend on the desire of the operator and the need for various information to encompass a polyp and to sometimes manipulate it. Desirably the polyp is captured by the loop 14 at its stalk portion if one is present. The loop 14 is then made smaller to snugly snare the polyp's stalk. This is accomplished by moving the slide means backwards to withdraw a further portion of the cable. Before the slide means are retracted completely, they should be preferably locked together by means of the hinged wire 57. Thereafter a conventional and known cauterizing current is supplied to the wire through connector 52. Of course, provision has previously been made to properly ground the patient. A combination of the cauterizing current and further diminution of the loop will resect the polyp which can then be removed by suitable and conventional means as by a suction means which may be a part of the colonscope equipment.

In the event that the polyp does not have a stalk or the polyp is quite large, it may be necessary to slice successive pieces of the polyp with cauterization accomplished each time. The ability to control the loop both in size and presentment to the polyp is a valuable achievement of the present invention.

The present invention provides the capabilities of the Shinya-Wolf snare in a device that can be easily operated by an assistant or by the surgeon himself, using only one hand. It could be manufactured inexpensively and so could be produced as a disposable item, eliminating the time consuming cleaning process. The size of the cable used enables the operator to remove polyps using coagulating current only, relying on mechanical shearing by the cable to sever the stalk. It is not necessary to use cutting current thereby lessening the chance of severing the stalk before the large blood vessels are completely coagulated.

What is claimed is:

1. A surgical instrument having a snare in the form of a loop useful in performing colonoscopic polypectomy comprising:
   (a) an elongated flexibly bendable open ended sheath having proximal and distal ends;
   (b) a folded on itself flexible cable positioned in said sheath and capable of being reciprocatingly moved therein whereby a portion of the folded cable describes a loop and is capable of being selectively advanced to extend beyond the distal end of the sheath;
   (c) an elongated housing means having cable receiving means;
   (d) said sheath having its proximal end secured to said elongated housing and in alignment with said cable receiving means;
   (e) said double cable being of sufficient length whereby end portions of said cable extend beyond the proximal end of said sheath and into said cable receiving means in said housing means;
   (f) two linear drive means for said folded on itself cable, each including an elongated rigid longitudinally movable means each having handle means;
   (g) guide means on said housing adapted and constructed to permit independent reciprocating motion of each of said elongated rigid longitudinally movable means;
   (h) one end portion of said cable being attached to one of said elongated rigid longitudinally movable means of said linear drive means and the other end portion of said cable being attached to the other of said elongated longitudinally movable means of said linear drive means whereby movement of said elongated rigid longitudinally movable means will selectively advance or withdraw said cable through the distal end of said sheath thereby controlling the size of the loop and relative movement of one of said elongated rigid longitudinally movable means relative to the other will control the configuration of the loop and selective means is provided whereby said two linear drive means may be locked together so that said linear drive means may be moved in unison.

2. The instrument of claim 1 wherein at least one of said first two elongated tubular means includes electrical connecting means for radio frequency energy.

3. The instrument of claim 2 wherein means is included to mount said instrument to a colonoscope.

4. The instrument of claim 1 wherein the means of "g" include two elongated retaining channel means alongside the rearward portion of said housing whereby each of said drive means is slidably secured.

5. The instrument of claim 4 wherein the housing is provided with finger retaining means.

6. The instrument of claim 5 wherein the first and second elongated tubular means is constructed of stainless steel.

7. The instrument of claim 6 wherein the said cable is constructed of braided stainless steel wires.

8. The instrument of claim 7 wherein the end portions of said cable are secured to each of said second elongated tubular means by crimping.

* * * * *